(12) United States Patent
Zhang et al.

(10) Patent No.: US 12,252,695 B1
(45) Date of Patent: Mar. 18, 2025

(54) PEONY PoWOX4 GENE AND APPLICATIONS OF CODED PROTEIN THEREOF

(71) Applicant: INTERNATIONAL CENTRE FOR BAMBOO AND RATTAN, Beijing (CN)

(72) Inventors: Wenbo Zhang, Beijing (CN); Yanting Chang, Beijing (CN); Yanjun Ma, Beijing (CN); Tao Hu, Beijing (CN); Zehui Jiang, Beijing (CN); Yayun Deng, Beijing (CN); Yufei Meng, Beijing (CN); Xue Zhang, Beijing (CN); Mengsi Xia, Beijing (CN)

(73) Assignee: INTERNATIONAL CENTRE FOR BAMBOO AND RATTAN, Beijing (CN)

( * ) Notice: Subject to any disclaimer, the term of this patent is extended or adjusted under 35 U.S.C. 154(b) by 0 days.

(21) Appl. No.: 18/887,121

(22) Filed: Sep. 17, 2024

(30) Foreign Application Priority Data

Feb. 1, 2024 (CN) .......................... 202410140139.X

(51) Int. Cl.
  *C12N 15/82* (2006.01)
  *C07K 14/415* (2006.01)
(52) U.S. Cl.
  CPC .......... *C12N 15/827* (2013.01); *C07K 14/415* (2013.01)
(58) Field of Classification Search
  None
  See application file for complete search history.

(56) References Cited

U.S. PATENT DOCUMENTS 11,198,885 B1   12/2021   Claeys

FOREIGN PATENT DOCUMENTS

| CN | 109355297 A | 2/2019 |
|----|-------------|--------|
| CN | 114958869 A | 8/2022 |
| CN | 116529377 A | 8/2023 |

OTHER PUBLICATIONS

Xia et al. "A preliminary investigation on the function validation and interactions of PoWOX4 genes in peony (*Paeonia ostii*)" 2022 Horticulturae 8(266): 22 total pages. (Year: 2022).*
Wang Yanyan, et al., Heterologous expression of tree peony (*Paeonia suffruticosa*) Squamosa promoter-binding protein-like (PsSPL) gene in *Arabidopsis thaliana* affects the vegetative growth and flowering time. Journal of Plant Physiology, vol. 52, No. 08, pp. 1207-1213 Date of issue: Aug. 20, 2016. (abstract) Full text, Claims involved: 1-8.
Notification to Grant Patent Right for Invention dated Jun. 7, 2024 in SIPO application No. 202410140139.X.
Searh report dated Jun. 3, 2024 in SIPO application No. 202410140139. X.

* cited by examiner

*Primary Examiner* — Matthew R Keogh
*Assistant Examiner* — Rebecca Stephens
(74) *Attorney, Agent, or Firm* — Pilloff Passino & Cosenza LLP; Rachel Pilloff; Sean Passino

(57) ABSTRACT

Disclosed are a peony PoWOX4 gene and applications of a coded protein thereof, belonging to the field of biotechnology. According to the present disclosure, *Arabidopsis thaliana* is taken as a model plant, and the peony PoWOX4 gene is transformed into *Arabidopsis thaliana* to promote the early bolting, flowering and vegetative growth of *Arabidopsis thaliana*.

4 Claims, 11 Drawing Sheets

Specification includes a Sequence Listing.

PEONY PoWOX4 GENE AND APPLICATIONS OF CODED PROTEIN THEREOF

CROSS-REFERENCE TO RELATED APPLICATIONS

This application claims priority to Chinese Patent Application No. 202410140139.X, filed on Feb. 1, 2024, the contents of which are hereby incorporated by reference.

INCORPORATION BY REFERENCE STATEMENT

This statement, made under Rules 77(b)(5)(ii) and any other applicable rule incorporates into the present specification of an XML file for a "Sequence Listing XML" (see Rule 831(a)), submitted via the USPTO patent electronic filing system or on one or more read-only optical discs (see Rule 1.52(e)(8)), identifying the names of each file, the date of creation of each file, and the size of each file in bytes as follows:
File name: PPH-US 2024-8683 Sequence.xml
Creation date: Sep. 11, 2024
Byte size: 17,238

TECHNICAL FIELD

The present application relates to the field of biotechnology, and in particular to a peony PoWOX4 gene and applications of a coded protein thereof.

BACKGROUND

As a superfamily of homeobox (HB) transcription factors in eukaryotic organisms, the WUSCHEL-related homeobox (WOX) family are plant-specific transcription factors with homeodomain (HD) that is conserved and identifiable and bindable by specific DNA sequences, and the homeodomain has a helix-turn-helix structure folded by 60-66 amino acids. According to the comprehensive study against the *Arabidopsis thaliana* genome by Haecker et al., it is revealed that there are a total of 15 genes grouped into three subdivisions in the WOX gene family of *Arabidopsis thaliana*, namely: the evolutionary branch/WUS branch (WUS and WOX1-7), the intermediate branch (WOX8-9 and WOX11-12), and the ancient branch (WOX10 and WOX13-14). There are other functional elements in addition to HD contained in members of each subdivision, for example, members of the evolutionary branch contain a specific WUS-box (T-L-X-L-F-P-X-X, with X representing any amino acid), with T-L being the starting amino acid, and the starting amino acid is not fixed in the ancient and intermediate branches.

WOX gene participates in plant somatic embryogenesis and meristematic tissue formation, and forms a regulatory network for plant somatic embryogenesis together with SERK (somatic embryogenesis receptor kinase), a cell-specific marker gene that is thought to be embryogenic, BABY BOOM (BBM), which plays a role in promoting cell division, as well as LEC1, a major regulator of embryogenesis and regulator of the activation of other members of the Leafy Cotyledon (LEC) gene family (LEC2, FUS3 and ABI3). With redundant functions, the members of the WOX gene family, which are compensatory and specific, are at the key position of the regulatory network pathway and belong to the key node genes in the regulatory network of plant somatic embryogenesis.

It has been shown that the members of the WOX family are functionally extensive, serving in a variety of processes such as the formation of apical meristematic tissues, maintenance of stem cells, formation of lateral and floral organs, embryonic development, hormone signaling, and metabolism of resistance to stress, and are particularly important in the regulation of regions of intense cell proliferation and differentiation. WOX4 has an important regulatory role in formation layer stem cells. *Arabidopsis thaliana* AtWOX4 promotes the development of the primordial formation layer, regulates lateral plant growth, and is involved in the regulation of vascular cell division. Although significant progress has been made in recent years regarding the function and mechanism of WOX genes in plant regeneration from scratch using *Arabidopsis thaliana* and other herbaceous species, fewer studies have been reported in woody plants, and functional studies on the peony WOX4 gene family have not yet been reported across the world.

As one of the important ways of plant regeneration in vitro, somatic embryogenesis is an effective way of rapid reproduction and is the major focus of peony tissue culture in the future. Currently, studies on functional genes in peony are mainly confined to flower and leaf color, flower pattern, flowering time, stress resistance, postharvest, bud dormancy and seed dormancy, while little research has been done on genes related to somatic embryogenesis in peony. The WOX gene family are key node genes in the regulatory network pathway of plant somatic embryogenesis. Therefore, it is of great significance to investigate the functional properties of embryonic genes WOX and the expression characteristics throughout the process of direct somatic embryogenesis and in various tissues of overexpressing *Arabidopsis thaliana* for the establishment of a complete system of peony plant regeneration and genetic transformation.

SUMMARY

In order to solve the problems existing in the prior art, the present disclosure provides a peony PoWOX4 gene and applications of a coded protein thereof, whereby *Arabidopsis thaliana* is taken as a model plant, and the expression characteristics of the PoWOX4 gene in various tissues expressing *Arabidopsis thaliana* are explored so as to provide a certain theoretical basis for establishing a complete plant regeneration and genetic transformation system for peony.

In order to achieve the above objectives, the present disclosure provides the following technical schemes.

The present disclosure provides a peony PoWOX4 gene and an application of a coded protein thereof in promoting early bolting and flowering of *Arabidopsis thaliana*, where a nucleotide sequence of the peony PoWOX4 gene is shown in SEQ ID NO. 7; and an amino acid sequence of a protein encoded by the peony PoWOX4 gene is shown in SEQ ID NO. 8.

The present disclosure also provides a method for promoting early bolting and flowering of *Arabidopsis thaliana*, including following steps: introducing the peony PoWOX4 gene into *Arabidopsis thaliana* to obtain a transgenic *Arabidopsis thaliana* plant stably expressing the peony PoWOX4 gene, and making the transgenic *Arabidopsis thaliana* plant bolting and blooming early; where a nucleotide sequence of the peony PoWOX4 gene is shown in SEQ ID NO. 7.

The present disclosure also provides an application of the peony PoWOX4 gene and a coded protein thereof in promoting vegetative growth of *Arabidopsis thaliana*, where a nucleotide sequence of the peony PoWOX4 gene is shown in SEQ ID NO. 7; and an amino acid sequence of a protein encoded by the peony PoWOX4 gene is shown in SEQ ID NO. 8.

Optionally, the promoting of vegetative growth of *Arabidopsis thaliana* includes promoting plant height growth of *Arabidopsis thaliana*.

The present disclosure also provides a method for promoting vegetative growth of the *Arabidopsis thaliana*, including following steps: introducing peony PoWOX4 gene into *Arabidopsis thaliana* to obtain a transgenic *Arabidopsis thaliana* plant stably expressing the peony PoWOX4 gene, and promoting the vegetative growth of the transgenic *Arabidopsis thaliana* plant; where a nucleotide sequence of the peony PoWOX4 gene is shown in SEQ ID NO. 7.

Optionally, the vegetative growth includes plant height growth.

The present disclosure also provides an application of the peony PoWOX4 gene and a coded protein thereof in regulating somatic embryogenesis of *Arabidopsis thaliana*, where the peony PoWOX4 gene is over-expressed to inhibit stem callus formation of the *Arabidopsis thaliana*;

a nucleotide sequence of the peony PoWOX4 gene is shown in SEQ ID NO. 7; and an amino acid sequence of a protein encoded by the peony PoWOX4 gene is shown in SEQ ID NO. 8.

The present disclosure also provides a method for regulating somatic embryogenesis of *Arabidopsis thaliana*, including following steps: overexpressing peony PoWOX4 gene in *Arabidopsis thaliana* to inhibit stem callus formation of the *Arabidopsis thaliana*;

where a nucleotide sequence of the peony PoWOX4 gene is shown in SEQ ID NO. 7; and an amino acid sequence of a protein encoded by the peony PoWOX4 gene is shown in SEQ ID NO. 8.

The present disclosure achieves the following technical effects.

According to present disclosure, the peony PoWOX4 gene is cloned from the cultivated *Paeonia ostii* 'Fengdan', and by analyzing the sequence and phylogenetic tree, it is determined that it belongs to the modern branch of the WOX gene family. After transforming into *Arabidopsis thaliana*, it is found by phenotypic comparison that peony PoWOX4 gene may promote early bolting, flowering and vegetative growth of *Arabidopsis thaliana*. The induction of callus using PoWOX4 transgenic *Arabidopsis thaliana* reveals that callus form in both leaves and roots but not in stems, and that there is no fluorescent expression in roots and leaves that form callus, whereas there is fluorescent expression in stems that do not form callus. According to the present disclosure, *Arabidopsis thaliana* is taken as a model plant, and by exploring the expression characteristics of PoWOX4 gene in various tissues of overexpressed *Arabidopsis thaliana*, a certain theoretical basis is provided for establishing a complete plant regeneration and genetic transformation system of peony.

BRIEF DESCRIPTION OF THE DRAWINGS

In order to explain the embodiments of the present disclosure or the technical scheme in the prior art more clearly, the drawings needed in the embodiments are briefly introduced below. Obviously, the drawings described below are only some embodiments of the present disclosure, and other drawings may be obtained according to these drawings without creative work for ordinary people in the field.

DETAILED DESCRIPTION OF THE EMBODIMENTS

Figure 1:
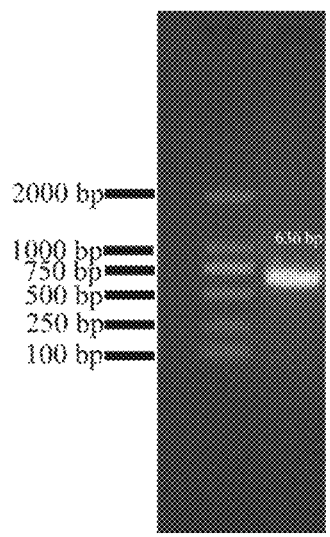
FIG. 1 is a polymerase chain reaction (PCR) electrophoresis diagram of peony PoWOX4 gene.

A number of exemplary embodiments of the present disclosure will now be described in detail, and this detailed description should not be considered as a limitation of the present disclosure, but should be understood as a more detailed description of certain aspects, characteristics and embodiments of the present disclosure.

It should be understood that the terminology described in the present disclosure is only for describing specific embodiments and is not used to limit the present disclosure. In addition, for the numerical range in the present disclosure, it should be understood that each intermediate value between the upper limit and the lower limit of the range is also specifically disclosed. Intermediate values within any stated value or stated range, as well as each smaller range between any other stated value or intermediate values within the stated range are also included in the present disclosure. The upper and lower limits of these smaller ranges may be independently included or excluded from the range.

Unless otherwise specified, all technical and scientific terms used herein have the same meaning as commonly understood by one of ordinary skill in the art to which this present disclosure relates. Although the present disclosure only describes the preferred methods and materials, any methods and materials similar or equivalent to those described herein can also be used in the practice or testing of the present disclosure. All documents mentioned in this specification are incorporated by reference to disclose and describe methods and/or materials related to the documents. In case of conflict with any incorporated document, the contents of this specification shall prevail.

It is obvious to those skilled in the art that many improvements and changes may be made to the specific embodiments of the present disclosure without departing from the scope or spirit of the present disclosure. Other embodiments will be apparent to the skilled person from the description of the present disclosure. The description and example of that present disclosure are exemplary only.

The terms "including", "comprising", "having" and "containing" used in this specification are all open terms, which means including but not limited to.

Embodiments

I. Experimental Methods
1. Materials

The material is cultivated peony (*Paeonia ostii*, or 'Fengdan'), and the seeds are purchased from the peony nursery in Heze, Shandong Province of China. Full and glossy seeds of 'Fengdan' with round shape are selected and soaked in water at room temperature for 2-3 days, then the outer skins of the seeds are peeled off and the seeds are then rinsed with running water for 2 hours (h), sterilized with 75% alcohol for 30 seconds (s), washed with sterile water for 3-5 times, sterilized with 2% sodium hypochlorite solution for 20 minutes (min), washed with sterile water for 3-5 times, and the surface water is drained off, and then the seed embryos are stripped off and placed in *Paeonia ostii* somatic embryo induction medium for somatic embryo induction culture, which is used for subsequent gene cloning and functional studies of its overexpression in *Arabidopsis thaliana*. The Columbia wild-type (Col-0) *Arabidopsis thaliana* is used as the transgenic material and cultured in pots in an artificial climate chamber with a light/dark cycle of 16 h/8 h, a temperature of 24±1 degrees Celsius (° C.), and a relative humidity of approximately 60-70%.

2. Methods
2.1 Synthesis of Total RNA and cDNA

Using Quick RNA Isolation Kit (Huayueyang Biotechnology (Beijing) Co., Ltd, China), the tissue culture seedlings of aseptic *Paeonia ostii* are used to extract RNA, and the concentration of RNA is determined by spectrophotometer. After the integrity of RNA bands is determined by 1% agarose gel electrophoresis, the RNA is stored in the ultra-low temperature refrigerator at −80° C. for later use. The extracted RNA is used as a template to synthesize the first strand of cDNA by reverse transcription according to the steps of Reverse Transcription System (A3500, Promega).

2.2 Cloning of *Paeonia ostii* PoWOX4 Gene

The primers (Table 1) are designed by SnapGene (V2.3.2) software according to the principle of primer design. With cDNA as the template, the target sequence is amplified by the high-fidelity enzyme (TaKaRa, Kusatsu, Japan) of LA Taq kit, and detected by 1% agarose gel electrophoresis, where the target sequence is obtained when the length of the target band is consistent with that of the marker sequence, and the CDS sequence of the *Paeonia ostii* PoWOX4 gene is obtained by cloning. Gel cutting is carried out on an ultraviolet gel cutting table, and the product is recovered according to the steps of DNA purification and recovery kit (Tiangen Biotech (Beijing) CO., LTD., China). The gel recovered products are connected with cloning vectors by using pMD19-T Vector Cloning Kit (TaKaRa, Kyoto, Japan), and the connection system is connected for more than half an hour for transformation. DH5α competent cells of *Escherichia coli* are transformed according to the steps of pMD19-T Vector Cloning Kit (TaKaRa, Kusatsu, Japan), then evenly coated on LB solid agar medium containing ampicillin (AMP), and monoclonal clones are selected for colony PCR after inverted culture at 37° C. for 12-16 h, positive single clones are shaken and plasmids are extracted by TIAN prep Mini Plasmid Kit (DP103-03, Tiangen Biotech (Beijing) CO., LTD., China) and 10 microliter (μL) plasmid solution is sent to Anshengda (Beijing, China) for sequencing, and the correct target sequences are obtained after verification.

TABLE 1

Primer sequences

| Genes | Primer sequence F (5'-3') | Primer sequence R (5'-3') |
| --- | --- | --- |
| PoWOX4 | ATGTATATGATGGGTTAT AATGATGGCGGAG (SEQ ID NO. 1) | ATTCCTCAACGGAAGGAA CTCAAAATACT (SEQ ID NO. 2) |
| Q-PoWOX4 | CGTTGGCGGCAATGAAGA AGAATC (SEQ ID NO. 3) | GGCAATTAGGAGGACTCA AGTTGGTAT (SEQ ID NO. 4) |
| Q-AtActin | GGTATGGGTCAGAAAGAT GCT (SEQ ID NO. 5) | CGTTGTAGAAAGTGTGAT GCC (SEQ ID NO. 6) |

2.3 Bioinformatics Analysis

The basic physicochemical properties of *Paeonia ostii* PoWOX4 sequence are analyzed using ProtParam (ExPASy-ProtParam tool), the secondary structure of PoWOX4 protein is analyzed using SOPMA (https://npsa-prabi.ibcp.fr/cgi-bin/npsa_automat.pl?page=npsa_sopma.html), and the subcellular localization of PoWOX4 protein is predicted using Plant-mPLoc (Plant-mPLoc server (sjtu.edu.cn)).

The WOX protein sequences of *Arabidopsis thaliana, Oryza sativa, Juglans regia, Vitis vinifera, Populus trichocarpa, Amborella trichopoda, Theobroma cacao, Picea abies, Selaginella moellendorffii, Ceratopteris richardii, Ginkgo biloba* and *Ostreococcus lucimarinus* are obtained by homologous search from Ensembl Plants, Plant Transcription Factor Database *PlantTFDB, PlantTFDB-Plant Transcription Factor Database@CBI, PKU (gao-lab.org)) and public database NCBI (National Center for Biotechnology Information) (nih.gov), followed by Multiple sequence comparison using Clustal W; using MEGA 11 software with the neighbor-joining method and 1,000 bootstrap replicates, with other parameters as default settings, a phylogenetic tree is constructed for the obtained WOX protein sequences of all the species together with the *Paeonia ostii* PoWOX4 protein sequence. Based on the complete amino acid sequence of WOX, the WOX target gene of *Paeonia ostii* is named according to the branching result of phylogenetic tree.

The amino acid sequences of WOX4 proteins in *Arabidopsis thaliana*, *Oryza sativa*, *Juglans regia*, *Vitis vinifera*, *Populus trichocarpa* and *Paeonia ostii* are compared and analyzed by DNAMAN software. The online website WEBLOGO (http://weblogo.berkeley.edu/logo.cgi) is used to draw the sequence identification map.

2.4 Functional Verification of Transforming *Paeonia ostii* PoWOX4 Gene into *Arabidopsis thaliana*

PoWOX4 gene is cloned into plant expression vector pBI121, and transgenic *Arabidopsis thaliana* plants genetically stably overexpressing 35S::PoWOX4 are obtained by *Agrobacterium*-mediated inflorescence infection. Overexpressed transgenic *Arabidopsis thaliana* of T3 generation and wild-type control are planted and cultured under the same culture conditions.

2.5 Fluorescence Quantitative Analysis

Tissues from root, stem, leaf, flower and fruit of *Arabidopsis thaliana* transcribed with PoWOX4 gene of T3 generation are taken and subjected to reverse transcription of the 1st strand of cDNA after extracting RNA, followed by 10-fold dilution in ddH$_2$O as a template, and the primers in Table 1 are used to complete the reaction on a QTOWER real-time fluorescence quantitative PCR instrument (analytik jena, Germany) using the TB Green Premix Ex Taq II Fluorescence Quantification Kit (Tli RNaseH Plus, TaKaRa). The PCR reaction system is TB Green Premix Ex Taq 5 µL; Template 1 µL; Primer (F+R) 0.4 µL, and ddH$_2$O replenished to 10 µL, with a total of 3 biological replicates set up, and the reaction conditions are pre-denaturation of 95° C. for 90 s; denaturation of 95° C. for 5 s, and unchaining of 60° C. for 30 s, 40 cycles; the dissolution curve of 60 to 95° C., with 1° C. temperature increase every 15 s. The relative expression of PoWOX4 in each part of the tissues is analyzed by using AtActin as the internal reference gene and the expression in *Arabidopsis thaliana* root tissues as the control group, and the relative expression is calculated by the $2^{-\Delta\Delta CT}$ method.

II. Results and Analysis

1. Clone and Sequence Analysis of *Paeonia ostii* PoWOX4 Gene

The nucleotide sequence of *Paeonia ostii* PoWOX4 with the expected length is shown in FIG. 1, and the length of its CDS sequence is 636 bp. The sequencing results show that the nucleotide sequence of *Paeonia ostii* PoWOX4 gene is as shown in SEQ ID NO. 7.

SEQ ID NO. 7:
ATGGGAAACATGAAGGTTCATCAGTTCGCACGTGGATTCTGGGAGCACG

AACCCTCCCTCACGCTTGGCTGCAAACGCCTTCGCCCACTTGCTCCCAA

ACTAATCAACAACGTCGATGGTGTCTCTTCTTTTGATCTCAAGAGCTTC

ATTAGACCTGAGAGCAGACCCATAAAGATTGGTCCCTCTCATGATAACA

GAGAGTCAGCTCAGATGGAAACACACCCAGGAGGGACAAGGTGGAACCC

AACACAAGAGCAGATAGGGATACTGGAGATGTTATATAGGGGCGGAATG

CGAACTCCTAATGCCCAACAAATAGAACAAATCACTTCTCAGCTGGCCA

-continued
AGTATGGCAAGATTGAAGGGAAGAATGTGTTCTATTGGTTCCAAAATCA

CAAAGCACGCGAGAGGCAGAAGCAAAACCGCAACAGTCTTGGTCTTAGC

CATTGTCCAAGGACCCCAGCCGCCACCACTAGCCCTTTGAGTACCATGG

GAGAAGTGGAAAGAGATCGAGAAGTTAGTCCGTACAAGAGGAAGGTCAG

GAGCTGGGGTTTTGAATGTGTGGAAGAGGTGAGATGTAGAGATGAGGAA

GGAGATAAGACTTTGGAGCTTTTTCCATTACACCCGGAAGGAAGATGA.

The basic physicochemical properties of the *Paeonia ostii* PoWOX4 gene are analyzed, with an open reading frame of 633 bp, encoding 211 amino acids, a relative molecular mass of about 24.30 kDa, a theoretical isoelectric point of 9.36, an instability coefficient II of 47.58, a total average hydrophilicity of −0.91, and a lipid coefficient of 60.52, making this protein presumably an unstable hydrophilic protein. The amino acid sequence of *Paeonia ostii* PoWOX4 is shown in SEQ ID NO. 8.

SEQ ID NO. 8:
MGNMKVHQFARGFWEHEPSLTLGCKRLRPLAPKLINNVDGVSSFDLKSF

IRPESRPIKIGPSHDNRESAQMETHPGGTRWNPTQEQIGILEMLYRGGM

RTPNAQQIEQITSQLAKYGKIEGKNVFYWFQNHKARERQKQNRNSLGLS

HCPRTPAATTSPLSTMGEVERDREVSPYKRKVRSWGFECVEEVRCRDEE

GDKTLELFPLHPEGR.

Subcellular localization prediction of *Paeonia ostii* PoWOX4 protein reveals that it is localized in the nucleus. The secondary structure of *Paeonia ostii* PoWOX4 protein is analyzed by SOPMA, and it is found that the secondary structure of *Paeonia ostii* PoWOX4 protein consists of 25.41% α-helices, 6.63% β-folds, 4.42% extended strands, and 63.54% irregular coils.

2. Phylogenetic Tree Analysis of Peony PoWOX4 Protein

Figure 2:
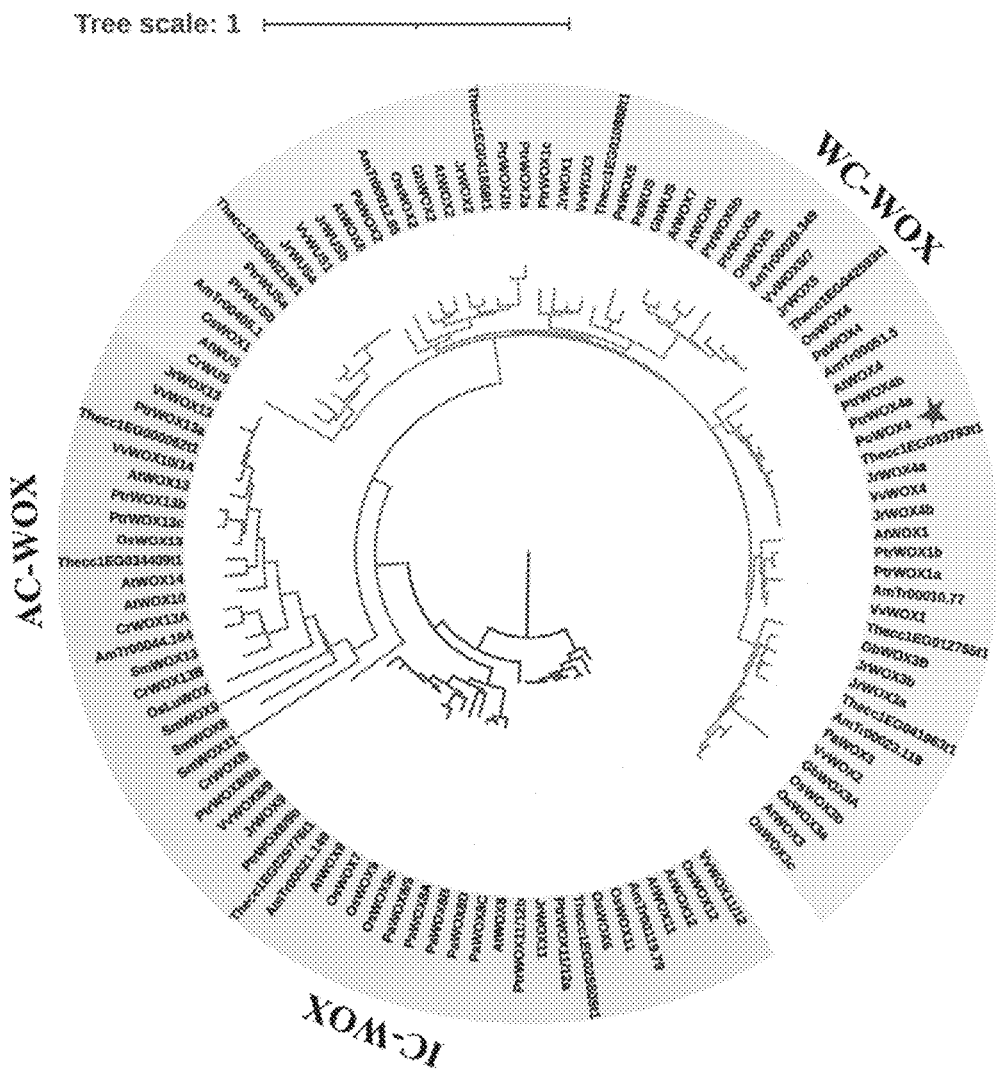
FIG. 2 shows the phylogenetic evolutionary tree of WOX genes in plants, where PoWOX4 is highlighted with a pentagram, JrWOX13 to SmWOX11 is AC-WOX, CrWOXB to VvWOX11/12 is IC-WOX, and CrWUS to OsWOX3c is WC-WOX.

In order to further understand the evolutionary relationship of *Paeonia ostii* PoWOX4 gene family, PoWOX4 gene is compared with 108 sequences from 12 species and the phylogenetic tree is constructed (FIG. 2). The full-length sequence of WOX protein is analyzed by NJ method with MEGA 11. A total of 109 WOX sequences from 13 species are divided into three branches: modern branch (WC-WOX), intermediate branch (IC-WOX) and ancient branch (AC-WOX). According to the evolutionary relationship, the WOX protein of *Paeonia ostii* is identified as PoWOX4, where the PoWOX4 is in the modern branch, which is closely related to *Theobroma cacao* and *Populus trichocarpa*.

Figure 3:
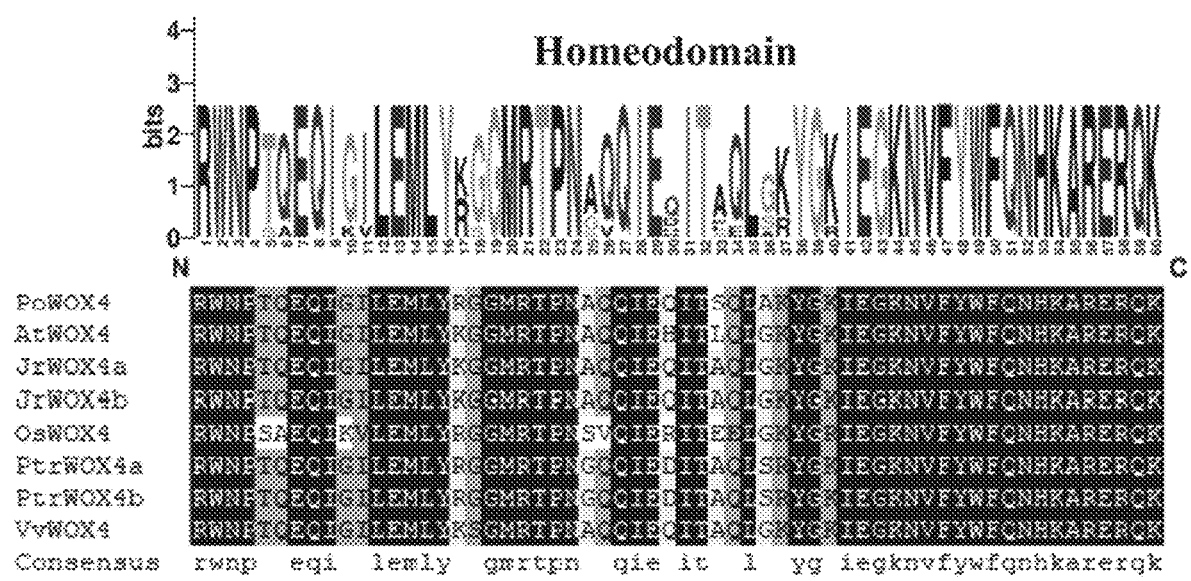
FIG. 3 shows multiple sequence comparison and sequence identity maps of WOX4 proteins in six species; where PoWOX4 sequence is shown as SEQ ID NO. 10, AtWOX4 sequence is shown as SEQ ID NO. 11, JrWOX4a sequence is shown as SEQ ID NO. 12, JrWOX4b sequence is shown as SEQ ID NO. 13, OsWOX4 sequence is shown as shown in SEQ ID NO. 14, PtrWOX4a sequence is as shown in SEQ ID NO. 15, PtrWOX4b sequence is as shown in SEQ ID NO. 16, and VvWOX4 sequence is as shown in SEQ ID NO. 17.

3. Multi-Sequence Alignment and Conserved Domain Analysis of *Paeonia ostii* PoWOX4 protein A total of 8 protein sequences of the same sub-branches of WOX4 from the model species, including *Arabidopsis thaliana*, *Oryza sativa* and *Juglans regia*, *Vitis vinifera* and *Populus trichocarpa*, are selected for multi-sequence comparison and analysis, and it is found that the peony PoWOX4 protein also contains the homologous heterodimeric structural domain HD and is highly conserved. The results of homology domain alignment show that there are many highly conserved residue sites in HD homology domain, among which the residue site of IEGKNVFYWFQNHKAR-ERQK (SEQ ID NO. 9) is highly conserved continuously, in which amino acid sequences indicated by dark black have 100% similarity, amino acid sequences indicated by dark grey have ≥75% similarity, and amino acid sequences indicated by light grey have similarity ≥50% (FIG. 3).

4. Phenotypic Analysis of *Arabidopsis thaliana* Overexpressing PoWOX4 Gene 4.1 Phenotype of PoWOX4 Transgenic *Arabidopsis thaliana*

Figure 4A:
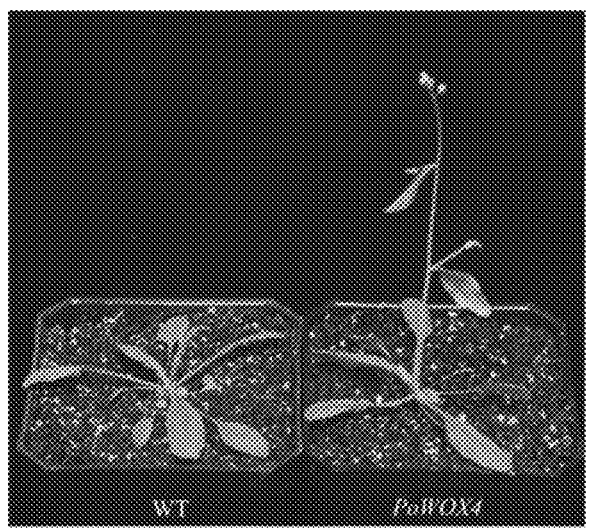
FIG. 4A shows the bolting and flowering of wild-type *Arabidopsis thaliana* (WT) and PoWOX4-overexpressed *Arabidopsis thaliana* (PoWOX4) on the 25th day.
Figure 4B:
FIG. 4B shows the bolting and flowering of wild-type *Arabidopsis thaliana* (WT) and PoWOX4-overexpressed *Arabidopsis thaliana* (PoWOX4) on the 29th day.

Heterologous expression and phenotypic analysis of PoWOX4 in *Arabidopsis thaliana* are carried out. In the phenotypic observation of transgenic *Arabidopsis thaliana*, it is found that under the same culture conditions, the PoWOX4 transgenic strain begins to bolt and bloom on the 25th day, and the plant height at flowering is significantly higher than that of the wild type, while the wild type begins to bolt and bloom on the 29th day. Compared with wild-type *Arabidopsis thaliana*, PoWOX4 transgenic strain has earlier flowering and higher plant height, suggesting that PoWOX4 may promote early bolting, flowering and vegetative growth of *Arabidopsis thaliana* (FIG. 4A and FIG. 4B).

4.2 Fluorescence Observation of PoWOX4 Transgenic *Arabidopsis thaliana*

Figure 5A:
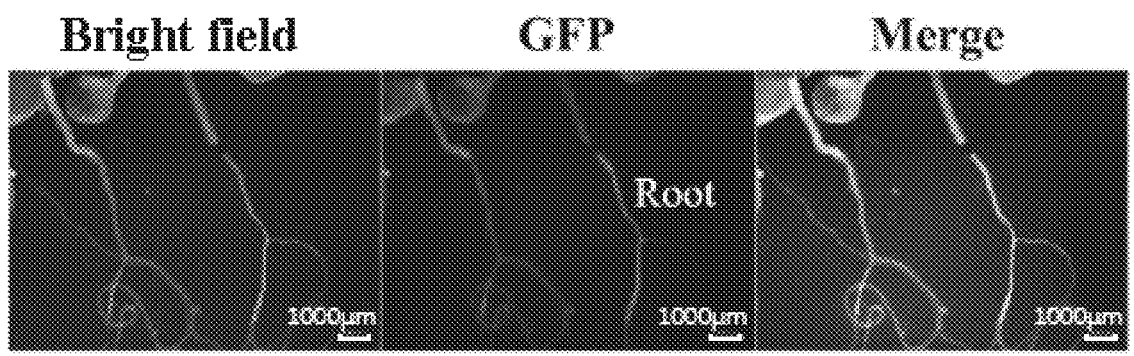
FIG. 5A is a diagram showing the fusion expression of PoWOX4 gene in root of transgenic *Arabidopsis thaliana* under microscope, in which the bright field, green fluorescent protein (GFP), and the bright field GFP merge are shown from left to right, and the green fluorescence shows the location of PoWOX4 fusion protein expression.
Figure 5B:
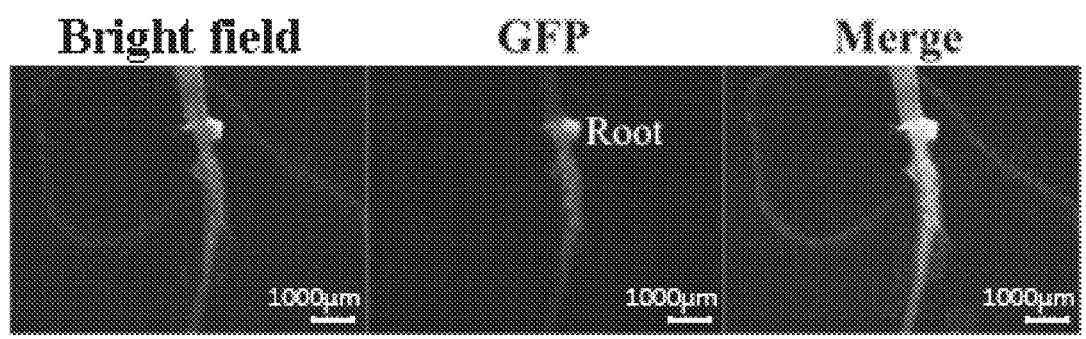
FIG. 5B is another diagram showing the fusion expression of PoWOX4 gene in root of transgenic *Arabidopsis thaliana* under microscope, in which the bright field, green fluorescent protein (GFP), and the bright field GFP merge are shown from left to right, and the green fluorescence shows the location of PoWOX4 fusion protein expression.
Figure 5C:
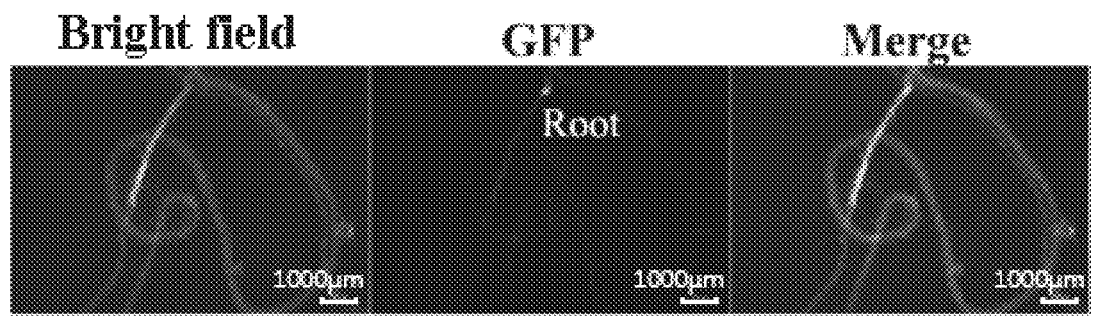
FIG. 5C is also a diagram showing the fusion expression of PoWOX4 gene in root of transgenic *Arabidopsis thaliana* under microscope, in which the bright field, green fluorescent protein (GFP), and the bright field GFP merge are shown from left to right, and the green fluorescence shows the location of PoWOX4 fusion protein expression.
Figure 5D:
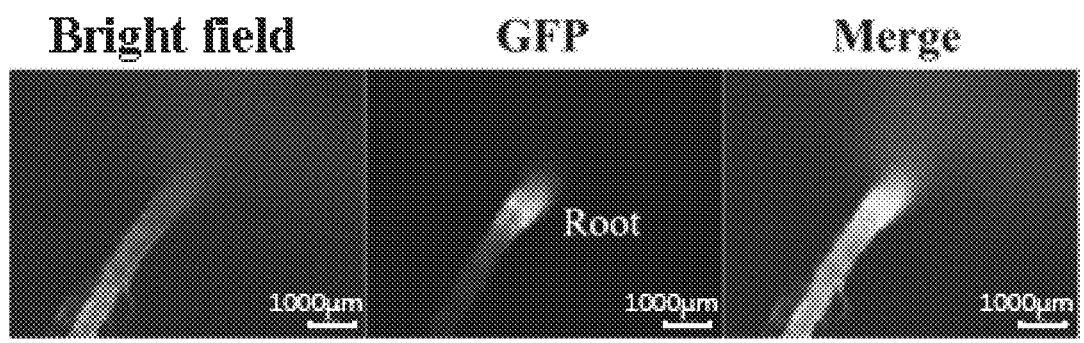
FIG. 5D is another diagram showing the fusion expression of PoWOX4 gene in root of transgenic *Arabidopsis thaliana* under microscope, in which the bright field, green fluorescent protein (GFP), and the bright field GFP merge are shown from left to right, and the green fluorescence shows the location of PoWOX4 fusion protein expression.
Figure 5E:
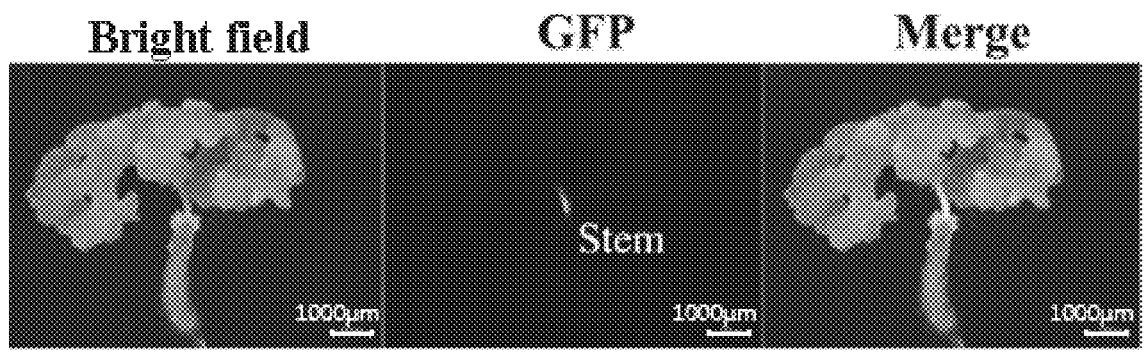
FIG. 5E shows the fusion expression of PoWOX4 gene in stem of transgenic *Arabidopsis thaliana* under microscope, in which the bright field, green fluorescent protein (GFP), and the bright field GFP merge are shown from left to right, and the green fluorescence shows the location of PoWOX4 fusion protein expression.

To investigate the reason for the phenotypic appearance of PoWOX4 transgenic *Arabidopsis thaliana*, the expression sites are observed, and it is found that PoWOX4 is expressed in the roots of transgenic *Arabidopsis thaliana* (FIG. 5A-FIG. 5D), and the fluorescence expression is especially stronger at the site of the growing point, indicating that the PoWOX4 gene is associated with root development. The induction of callus using PoWOX4 transgenic *Arabidopsis thaliana* seedlings reveals that both leaves and roots as culture materials are capable of forming callus, whereas no callus is formed by using the stem as culture material. By observing the fluorescence, it is found that there is no fluorescence expression in roots and leaves that form callus, whereas there is fluorescence expression in stems that do not form callus (FIG. 5E), which suggests that PoWOX4 expression decreases after the formation of callus in roots and leaves, whereas in stems it may not have promoted the formation of callus due to the high expression of PoWOX4.

5. Analysis of Expression Patterns

Figure 6:
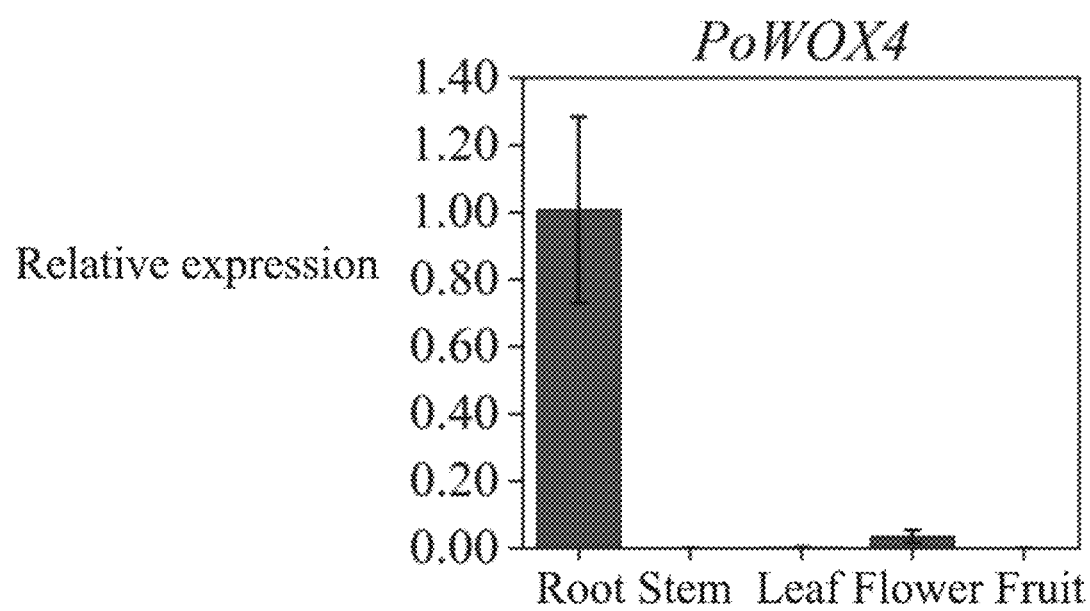
FIG. 6 shows the expression of PoWOX4 gene in different parts of transgenic *Arabidopsis thaliana*.

The expression of PoWOX4 gene in transgenic *Arabidopsis thaliana* in various parts of *Arabidopsis thaliana* tissues (roots, stems, leaves, flowers, and fruits) is analyzed by RT-qPCR (FIG. 6), and the results show that PoWOX4 has the highest expression in the roots, with less expression in the flowers, and is almost not expressed in the other three parts of *Arabidopsis thaliana*.

The above-mentioned embodiments only describe the preferred mode of the present disclosure, and do not limit the scope of the present disclosure. Under the premise of not departing from the design spirit of the present disclosure, various modifications and improvements made by ordinary technicians in the field to the technical scheme of the present disclosure shall fall within the protection scope determined by the claims of the present disclosure.

What is claimed is:

1. A method of promoting bolting early and flowering of early by an *Arabidopsis thaliana* plant, comprising: introducing a *Paeonia ostia* WUSCHEL-related homeobox 4 (PoWOX4) gene into an *Arabidopsis thaliana* plant to obtain a transgenic *Arabidopsis thaliana* plant that stably overexpresses the PoWOX4 gene, thereby making the transgenic *Arabidopsis thaliana* plant bolt early and flower early as compared to a control plant; wherein the PoWOX4 gene comprises a nucleotide sequence that encodes the amino acid sequence of SEQ ID NO: 8.

2. A method of increasing the vegetative growth by an *Arabidopsis thaliana* plant, comprising introducing a PoWOX4 gene into an *Arabidopsis thaliana* plant to obtain a transgenic *Arabidopsis thaliana* plant that stably overexpresses the PoWOX4 gene, and thereby increasing the vegetative growth by the transgenic *Arabidopsis thaliana* plant as compared to a control plant; wherein the PoWOX4 gene comprises a nucleotide sequence that encodes the amino acid sequence of SEQ ID NO: 8.

3. The method according to claim 2, wherein increasing the vegetative growth by the transgenic *Arabidopsis thaliana* plant causes increased plant height growth by the transgenic *Arabidopsis thaliana* plant as compared to a control plant.

4. A method of inhibiting stem callus formation by an *Arabidopsis thaliana* plant, comprising introducing a PoWOX4 gene into an *Arabidopsis thaliana* plant to obtain a transgenic *Arabidopsis thaliana* plant that stably overexpresses the PoWOX4 gene, and thereby inhibiting stem callus formation by the *Arabidopsis thaliana* plant as compared to a control plant; wherein the PoWOX4 gene comprises; a nucleotide sequence that encodes the amino acid sequence of SEQ ID NO: 8.

* * * * *

SEQUENCE LISTING

```
Sequence total quantity: 17
SEQ ID NO: 1            moltype = DNA  length = 31
FEATURE                 Location/Qualifiers
source                  1..31
                        mol_type = other DNA
                        organism = synthetic construct
SEQUENCE: 1
atgtatatga tgggttataa tgatggcgga g                                  31

SEQ ID NO: 2            moltype = DNA  length = 29
FEATURE                 Location/Qualifiers
source                  1..29
                        mol_type = other DNA
                        organism = synthetic construct
SEQUENCE: 2
attcctcaac ggaaggaact caaaatact                                     29

SEQ ID NO: 3            moltype = DNA  length = 24
FEATURE                 Location/Qualifiers
source                  1..24
                        mol_type = other DNA
                        organism = synthetic construct
SEQUENCE: 3
cgttggcggc aatgaagaag aatc                                          24

SEQ ID NO: 4            moltype = DNA  length = 27
FEATURE                 Location/Qualifiers
source                  1..27
                        mol_type = other DNA
                        organism = synthetic construct
SEQUENCE: 4
ggcaattagg aggactcaag ttggtat                                       27

SEQ ID NO: 5            moltype = DNA  length = 21
FEATURE                 Location/Qualifiers
source                  1..21
                        mol_type = other DNA
                        organism = synthetic construct
SEQUENCE: 5
ggtatgggtc agaaagatgc t                                             21

SEQ ID NO: 6            moltype = DNA  length = 21
FEATURE                 Location/Qualifiers
source                  1..21
```

```
                        mol_type = other DNA
                        organism = synthetic construct
SEQUENCE: 6
cgttgtagaa agtgtgatgc c                                            21

SEQ ID NO: 7            moltype = DNA   length = 636
FEATURE                 Location/Qualifiers
source                  1..636
                        mol_type = other DNA
                        organism = synthetic construct
SEQUENCE: 7
atgggaaaca tgaaggttca tcagttcgca cgtggattct gggagcacga accctccctc   60
acgcttggct gcaaacgcct tcgcccactt gctcccaaac taatcaacaa cgtcgatggt  120
gtctcttctt ttgatctcaa gagcttcatt agacctgaga gcagaccat aaagattgat  180
ccctctcatg ataacagaga gtcagctcag atgaaaacac cccaggagg gacaaggtgg  240
aacccaacac aagagcagat agggatactg gagatgttat ataggggcgg aatgcgaact  300
cctaatgccc aacaaataga acaaatcact tctcagctgg ccaagtatgg caagattgaa  360
gggaagaatg tgttctattg gttccaaaat cacaaagcac gcgagaggca gaagcaaaac  420
cgcaacagtc ttggtcttag ccattgtcca aggaccccag ccgccaccac tagcccttg   480
agtaccatgg gagaagtgga aagatcga gaagttagtc cgtacaagag gaaggtcagg   540
agctggggtt tgaatgtgt ggaagaggtg agatgtagag atgaggaagg agataagact  600
ttggagcttt tccattaca cccggaagga agatga                              636

SEQ ID NO: 8            moltype = AA  length = 211
FEATURE                 Location/Qualifiers
source                  1..211
                        mol_type = protein
                        organism = synthetic construct
SEQUENCE: 8
MGNMKVHQFA RGFWEHEPSL TLGCKRLRPL APKLINNVDG VSSFDLKSFI RPESRPIKIG   60
PSHDNRESAQ METHPGGTRW NPTQEQIGIL EMLYRGGMRT PNAQQIEQIT SQLAKYGKIE  120
GKNVFYWFQN HKARERQKQN RNSLGLSHCP RTPAATTSPL STMGEVERDR EVSPYKRKVR  180
SWGFECVEEV RCRDEEGDKT LELFPLHPEG R                                 211

SEQ ID NO: 9            moltype = AA  length = 20
FEATURE                 Location/Qualifiers
source                  1..20
                        mol_type = protein
                        organism = synthetic construct
SEQUENCE: 9
IEGKNVFYWF QNHKARERQK                                               20

SEQ ID NO: 10           moltype = AA  length = 84
FEATURE                 Location/Qualifiers
source                  1..84
                        mol_type = protein
                        organism = synthetic construct
SEQUENCE: 10
RWNPTQEQIG ILEMLYRGGM RTPNAQQIEQ ITSQLAKYGK IEGKNVFYWF QNHKARERQK   60
QNRNSLGLSH CPRTPAATTS PLST                                          84

SEQ ID NO: 11           moltype = AA  length = 89
FEATURE                 Location/Qualifiers
source                  1..89
                        mol_type = protein
                        organism = synthetic construct
SEQUENCE: 11
RWNPTQEQIG ILEMLYKGGM RTPNAQQIEH ITLQLGKYGK IEGKNVFYWF QNHKARERQK   60
QKRNNLISLS CQSSFTTTGV FNPSVTMKT                                     89

SEQ ID NO: 12           moltype = AA  length = 86
FEATURE                 Location/Qualifiers
source                  1..86
                        mol_type = protein
                        organism = synthetic construct
SEQUENCE: 12
RWNPTQEQIG ILEMLYKGGM RTPNAQQIEQ ITAQLGKYGK IEGKNVFYWF QNHKARERQK   60
QKRNSLGLGH CPRTPAPITT MITLET                                        86

SEQ ID NO: 13           moltype = AA  length = 85
FEATURE                 Location/Qualifiers
source                  1..85
                        mol_type = protein
                        organism = synthetic construct
SEQUENCE: 13
RWNPTQEQIG ILEMLYKGGM RTPNAQQIEQ ITAQLGKYGK IEGKNVFYWF QNHKARERQK   60
QKRSSLGLGH CPRTPVPITT ITLET                                         85

SEQ ID NO: 14           moltype = AA  length = 87
```

```
FEATURE             Location/Qualifiers
source              1..87
                    mol_type = protein
                    organism = synthetic construct
SEQUENCE: 14
RWNPSAEQIK VLEMLYRGGM RTPNSVQIER ITEELGKYGR IEGKNVFYWF QNHKARERQK   60
QKRAALLTLS TLDPSLLPAT ANETKEA                                      87

SEQ ID NO: 15       moltype = AA  length = 85
FEATURE             Location/Qualifiers
source              1..85
                    mol_type = protein
                    organism = synthetic construct
SEQUENCE: 15
RWNPTQEQIG ILEMLYRGGM RTPNGQQIED ITAQLSRYGK IEGKNVFYWF QNHKARERQK   60
QKRNSLGLSH SPRTPSPVTI ISLDT                                        85

SEQ ID NO: 16       moltype = AA  length = 85
FEATURE             Location/Qualifiers
source              1..85
                    mol_type = protein
                    organism = synthetic construct
SEQUENCE: 16
RWNPTQEQIG ILEMLYRGGM RTPNGQQIED ITAQLSRYGK IEGKNVFYWF QNHKARERQK   60
QKRNSLGLSH SPRTPSPITI ISLDT                                        85

SEQ ID NO: 17       moltype = AA  length = 85
FEATURE             Location/Qualifiers
source              1..85
                    mol_type = protein
                    organism = synthetic construct
SEQUENCE: 17
RWNPTQEQIG ILEMLYKSGM RTPNAQQIEQ ITAQLGKYGK IEGKNVFYWF QNHKARERQK   60
QKRNSLGLGH CPRTPTSITT ITLDT                                        85
```